(12) United States Patent
Schindler et al.

(10) Patent No.: US 6,613,772 B1
(45) Date of Patent: Sep. 2, 2003

(54) SUBSTITUTED 2-ARYL-4-AMINO-CHINAZOLINES, METHOD FOR THE PRODUCTION AND USE THEREOF AS MEDICAMENTS

(75) Inventors: Ursula Schindler, Bad Soden (DE); Karl Schönafinger, Alzenau (DE); Hartmut Strobel, Liederbach (DE); Peter Schindler, Bad Soden (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/581,763

(22) PCT Filed: Dec. 11, 1998

(86) PCT No.: PCT/EP98/08097
§ 371 (c)(1), (2), (4) Date: Jun. 16, 2000

(87) PCT Pub. No.: WO99/32460
PCT Pub. Date: Jul. 1, 1999

(30) Foreign Application Priority Data

Dec. 18, 1997  (DE) ......................................... 197 56 388

(51) Int. Cl.$^7$ ..................... C07D 239/94; A61K 31/517
(52) U.S. Cl. ............... 514/259; 514/217.06; 514/228.2; 514/232.5; 514/233.8; 514/247; 514/248; 514/249; 514/252.02; 514/252.11; 514/252.17; 514/255.05; 544/293; 544/116; 544/80; 544/58.6; 544/62; 544/263.21; 544/264; 544/235; 544/257; 540/600
(58) Field of Search ........................... 514/259, 255.05, 514/252.02, 247, 228.2; 544/293, 116, 80, 58.6, 62, 264, 235, 257, 263.21; 540/600

(56) References Cited

U.S. PATENT DOCUMENTS

| | | |
|---|---|---|
| 3,594,480 A | 7/1971 | Cronin et al. ............... 424/250 |
| 3,819,628 A | 6/1974 | Simpson et al. ..... 260/256.4 Q |
| 5,436,233 A | 7/1995 | Lee et al. ..................... 514/63 |

FOREIGN PATENT DOCUMENTS

| | | |
|---|---|---|
| DE | 2 338 669 | 2/1974 |
| EP | 0 655 456 A1 | 5/1995 |
| GB | 1390015 | 4/1975 |

OTHER PUBLICATIONS

R. L. McKee et al., "Some Basically Substituted Quinazolines," *J. Chem. Soc.*, vol. 68: 1902–3 (Oct. 1946).

A. Mülsch et al., "Purification of Heme–Containing Soluble Guanylyl Cyclase," *Methods in Enzymology*, vol. 195: 377–383 (1991).

Primary Examiner—John M. Ford
(74) Attorney, Agent, or Firm—Finnegan, Henderson, Farabow, Garrett & Dunner, L.L.P.

(57) ABSTRACT

Compounds of the formula I

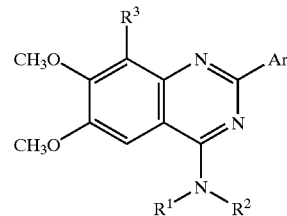

in which $R^1$, $R^2$, $R^3$ and Ar have the meanings indicated in the claims, are suitable for the production of pharmaceuticals, for example for the prophylaxis and therapy of cardiovascular diseases such as high blood pressure, angina pectoris, cardiac insufficiency, thromboses or atherosclerosis. The compounds of the formula I have the ability to modulate the endogenous production of cyclic guanosine monophosphate (cGMP) and are generally suitable for the therapy and prophylaxis of disease states which are associated with a disturbed cGMP balance.

11 Claims, No Drawings

SUBSTITUTED 2-ARYL-4-AMINO-CHINAZOLINES, METHOD FOR THE PRODUCTION AND USE THEREOF AS MEDICAMENTS

This is a 371 of PCT/EP98/08097, filed Dec. 11, 1998.

The present invention relates to compounds of the formula I

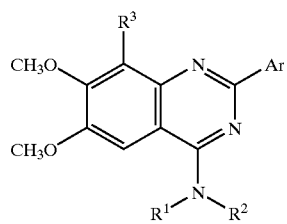

which are suitable for the production of pharmaceuticals, for example for the prophylaxis and therapy of cardiovascular conditions such as high blood pressure, angina pectoris, cardiac insufficiency, thromboses or atherosclerosis. The compounds of the formula I have the ability to modulate the endogenous production of cyclic guanosine monophosphate (cGMP) and are generally suitable for the therapy and prophylaxis of disease states which are associated with a disturbed cGMP balance.

Cyclic guanosine monosphosphate (cGMP) is an important intracellular messenger which, via the modulation of cGMP-dependent protein kinases, phosphodiesterases and ion channels, induces a large number of various effects. Examples are smooth muscle relaxation, the inhibition of platelet activation and the inhibition of smooth muscle cell proliferation and leukocyte adhesion. cGMP is produced by particulate and soluble guanylate cyclases as a response to a number of extra- and intracellular stimuli. In the case of the particulate guanylate cyclases, the stimulation essentially takes place by means of peptide signal substances, such as the atrial peptide or the cerebral natriuretic peptide. The soluble guanylate cyclases (sGC), which are cytosolic, heterodimeric heme proteins, however, are essentially regulated by a family of low molecular weight, enzymatically formed factors. The most important stimulant is nitrogen monoxide (NO) or a closely related species; the importance of other factors such as carbon monoxide or the hydroxyl radical is still largely unexplained. The binding of NO to the heme with formation of a pentacoordinated heme-nitrosyl complex is discussed as an activation mechanism. The release associated therewith of the histidine bound in the basal state to the iron converts the enzyme into the activated conformation. Active soluble guanylate cyclases are composed of one α- and one β-subunit each. A number of types of subunits are described, which differ from one another with respect to sequence, tissue-specific distribution and expression in various stages of development. The subtypes $\alpha_1$ and $\beta_1$ are mainly expressed in the brain and lung, while $\beta_2$ is mainly found in the liver and kidney. It was possible to detect the sub type $\alpha_2$ in human fetal brain; the subunits designated as $\alpha_3$ and $\beta_3$ were isolated from human brain and are homologous to $\alpha_1$ and $\beta_1$. More recent work indicates an $\alpha_2$ subunit, which contains an insert in the catalytic domain. All subunits exhibit great homology in the area of the catalytic domain. The enzymes presumably contain one heme per heterodimer, which is bonded via $\beta_1$-Cys-78 and/or $\beta_1$-His-105 and is part of the regulatory center.

Under pathological conditions, the formation of guanylate cyclase-activating factors can be decreased, or intensified degradation thereof can take place due to the increased occurrence of free radicals. The decreased activation of the sGC resulting from this leads via the reduction -of the respective cGMP-mediated cell response to a rise in the blood pressure, to platelet activation and to increased cell proliferation and cell adhesion. As a result, the development of endothelial dysfunction, atherosclerosis, high blood pressure, stable and unstable angina pectoris, thromboses, myocardial infarct, strokes or erectile dysfunction occurs.

The pharmacological stimulation of the sGC offers one possibility for the normalization of the cGMP production and thus allows the treatment or prevention of these diseases. For the pharmacological stimulation of the sGC, until now compounds such as, for example, nitrates were exclusively used, whose action is based on an intermediate release of NO. The disadvantage of this method of treatment lies in the development of tolerance and the higher dose which is therefore necessary.

Various quinazolines and pharmacological actions of quinazolines are already known. 2-(p-chlorophenyl)-4-(1-diethylamino-4-pentylamino)-6,7-dimethoxyquinazoline dihydrochloride has been published without indication of the potency in connection with compounds which have an antimalaria action (R. L. McKee, M. K. McKee and R. W. Bost, J. Amer. Chem. Soc. 68: 1902–1903 (1946)).

2-Alkylquinazolines have been described as bronchodilating and hypotensive compounds (U.S. Pat. No. 3,594,480). Specific 2-phenylquinazolines which contain nitrato groups in the 4-amino substituents have been described as antianginal agents (DE-A-2 338 669). 2-Arylquinazolines which contain phosphonato groups have additionally been described as agents for the treatment of hyperlipidemia, hypertension and diabetes (EP-A-0 655 456).

In the attempt to find efficacious compounds for the modulation of the endogenous production of cyclic guanosine monophosphate (cGMP), which are suitable for the therapy and prophylaxis of disease states which are associated with a disturbed cGMP balance, it has now been found that the quinazolines of the formula I bring about a strong activation of guanylate cyclase and are thus suitable for the treatment of diseases which are associated with a low cGMP level.

The present invention therefore relates to compounds of the formula I

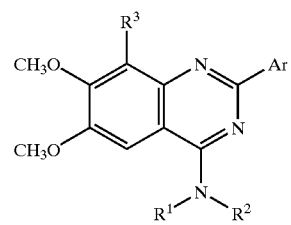

and/or stereoisomeric forms of the compounds of the formula I and/or mixtures of such forms in all ratios and/or physiologically tolerable salts of the compounds of the formula I, in which $R^1$ and $R^2$ are identical or different and independently of one another are
  1. hydrogen,
  2. $(C_1–C_5)$-alkyl,
  3. $(C_1–C_5)$-alkyl, which is mono-, di- or trisubstituted by
    3.1 —OH
    3.2 —O—$(C_1–C_6)$-alkyl, 3.3 —SH,
3.4 —SR$^4$, in which R$^4$ is (C$_1$–C$_6$)-alkyl,
3.5 —N(R$^6$)R$^7$, in which R$^6$ and R$^7$ are identical or different and independently of one another are hydrogen or (C$_1$–C$_6$)-alkyl,
3.6 —C(O)—N(R$^6$)R$^7$, in which R$^6$ and R$^7$ are identical or different and independently of one another are hydrogen or (C$_1$–C$_6$)-alkyl, or R$^6$ and R$^7$, together with the N atom to which they are bonded, form a morpholine, piperazine, imidazole, piperidine, pyrrolidine, thiomorpholine, 1-oxothiomorpholine, 1,1-dioxothiomorpholine or hexamethyleneimine radical,
3.7 —O—(C$_1$–C$_6$)-alkyl, which is mono-, di- or trisubstituted by
   3.7.1 —OH,
   3.7.2 —SH,
   3.7.3 =O,
   3.7.4 —COOH,
3.8 —COOH,
3.9 —C(O)—O—R$^8$, in which R$^8$ is (C$_1$–C$_6$)-alkyl,
3.10 phenyl,
3.11 phenyl, which is mono-, di- or trisubstituted by
   3.11.1 —O—(C$_1$–C$_4$)-alkyl,
   3.11.2 —O-phenyl,
   3.11.3 (C$_1$–C$_4$)-alkyl,
   3.11.4 —NO$_2$,
   3.11.5 halogen,
   3.11.6 —C(R$^9$)(R$^{10}$)R$^{11}$, in which R$^9$, R$^{10}$ and R$^{11}$ independently of one another are hydrogen or halogen,
3.12 a radical of a heterocycle from the group consisting of morpholine, piperazine, imidazole, piperidine, pyrrolidine, pyridine, thiomorpholine, 1-oxothiomorpholine, 1,1-dioxothiomorpholine, hexamethyleneimine, pyrrole, pyrazole, pyridazine, pyrazine, pyrimidine, indolizine, indole, indazole, purine, quinoxaline, furan, quinazoline, cinnoline, pteridine, oxazole, isoxazole, thiazole, isothiazole, furazan, indoline, pyrazoline, thiophene, xanthine, imidazoline and pyran,
3.13 a radical of a heterocycle described in 3.12, which is mono-, di-, tri- or tetrasubstituted by
   3.13.1 (C$_1$–C$_4$)-alkyl,
   3.13.2 =O,
   3.13.3 halogen,
   3.13.4 —O—(C$_1$–C$_4$)-alkyl,
   3.13.5 —NO$_2$,
4. (C$_3$–C$_7$)-cycloalkyl, which is unsubstituted or substituted by
   4.1 (C$_1$–C$_4$)-alkyl,
   4.2 —OH,
   4.3 —O—(C$_1$–C$_4$)-alkyl,
   4.4 —NH$_2$,
5. a radical of a heterocycle from the group consisting of morpholine, piperazine, imidazole, piperidine, pyrrolidine, pyridine, thiomorpholine, 1-oxothiomorpholine, purine, 1,1-dioxothiomorpholine, hexamethyleneimine, pyrrole, pyrazole, pyrazine, pyrimidine, pyridazine, indolizine, indole, indazole, quinoxaline, quinazoline, cinnoline, pteridine, oxazole, isoxazole, thiazole, isothiazole, furan, furazan, indoline, pyrazoline, thiophene, xanthine, imidazoline and pyran, where this heterocycle is unsubstituted or substituted by
   5.1 the radicals described under 3.1 to 3.13,
   5.2 (C$_1$–C$_6$)-alkyl,
   5.3 (C$_1$–C$_6$)-alkyl, which is substituted as described under 3.1 to 3.13,
or
R$^1$ and R$^2$ together with the N atom to which they are bonded, form a radical of a heterocycle from the group consisting of pyrrole, pyrrolidine, imidazole, pyrazole, piperidine, piperazine, morpholine, pyrazoline, imidazoline, thiomorpholine, thiazolidine, 1-oxothiomorpholine, 1,1-dioxothiomorpholine and hexamethyleneimine, where this heterocycle is unsubstituted or is substituted by
   1. the radicals described under 3.1 to 3.13,
   2. (C$_1$–C$_6$)-alkyl,
   3. (C$_1$–C$_6$)-alkyl, which is substituted as described under 3.1 to 3.13,
R$^3$ is is hydrogen or methoxy,
Ar is phenyl, which is mono-, di- or trisubstituted by
   1. halogen,
   2. —NO$_2$,
   3. —O—(C$_1$–C$_6$)-alkyl,
   4. (C$_1$–C$_6$)-alkyl, which is unsubstituted or is mono-, di- or trisubstituted by halogen,
   5. —CN,
   6. —C(O)—N(R$^{12}$)R$^{13}$, in which R$^{12}$ and R$^{13}$ are identical or different and independently of one another are hydrogen or (C$_1$–C$_6$)-alkyl,
where 2-(p-chlorophenyl)-4-((1-diethylamino-4-pentyl)amino)-6,7-dimethoxyquinazoline dihydrochloride and 2-(p-chlorophenyl-4-(4-hydroxybutyl)amino-6,7,8-trimethoxyquinazoline are excluded.
Preferred compounds of the formula I and/or stereoisomeric forms of the compounds of the formula I and/or mixtures of such forms in all ratios and/or physiologically tolerable salts of the compounds of the formula I are those in which
R$^1$ and R$^2$ are identical or different and independently of one another are
   1. hydrogen,
   2. (C$_1$–C$_3$)-alkyl,
   3. (C$_1$–C$_3$)-alkyl, which is mono-, di- or trisubstituted by
     3.1 —OH
     3.2 —O—(C$_1$–C$_3$)-alkyl,
     3.3 —N(R$^6$)R$^7$, in which R$^6$ and R$^7$ are identical or different and independently of one another are hydrogen or (C$_1$–C$_3$)-alkyl,
     3.4 —C(O)—N(R$^6$)R$^7$, in which R$^6$ and R$^7$ are identical or different and independently of one another are hydrogen or (C$_1$–C$_4$)-alkyl, or R and R, together with the N atom to which they are bonded, are a morpholine, piperazine, imidazole, piperidine, pyrrolidine, thiomorpholine, 1-oxothiomorpholine, 1,1-dioxothiomorpholine or hexamethyleneimine radical,
     3.5 —O—(C$_1$–C$_6$)-alkyl, which is monosubstituted by —OH,
     3.6 —COOH,
     3.7 —C(O)—O—R$^8$, in which R$^8$ is (C$_1$–C$_4$)-alkyl,
     3.8 phenyl,
     3.9 phenyl, which is mono-, di- or trisubstituted by
        3.9.1 —O—(C$_1$–C$_4$)-alkyl,
        3.9.2 —O-phenyl,
        3.9.3 (C$_1$–C$_4$)-alkyl,
        3.9.4 —NO$_2$,
     3.10 a radical of a heterocycle from the group consisting of morpholine, piperazine, imidazole, piperidine, pyrrolidine, pyridine, thiomorpholine, 1-oxothiomorpholine, 1,1-dioxothiomorpholine, hexamethyleneimine, pyrrole, pyrazole, purine and pyrimidine,
- 3.11 a radical of a heterocycle described in 3.10, which is mono-, di-, tri- or tetrasubstituted by
  - 3.11.1 ($C_1$–$C_4$)-alkyl,
  - 3.11.2 =O,
- 4. ($C_5$–$C_6$)-cycloalkyl, which is unsubstituted or is substituted by
  - 4.1 ($C_1$–$C_4$)-alkyl,
  - 4.2 —OH,
  - 4.3 —O—($C_1$–$C_4$)-alkyl,
  - 4.4 —$NH_2$,
- 5. a radical of a heterocycle from the group consisting of pyrrole, pyrrolidine, imidazole, pyrazole, pyridine, pyrazine, pyrimidine, pyridazine, oxazole, isoxazoline, thiazole, isothiazole, piperidine, piperazine, morpholine, pyrazoline, imidazoline, thiomorpholine, thiazolidine, 1-oxothiomorpholine, 1,1-dioxothiomorpholine and hexamethyleneimine, where this heterocycle is unsubstituted or is mono-, di- or trisubstituted by
  - 5.1 the radicals described under 3.1 to 3.11,
  - 5.2 ($C_1$–$C_6$)-alkyl,
  - 5.3 ($C_1$–$C_6$)-alkyl, which is substituted as described under 3.1 to 3.11, or $R^1$ and $R^2$ together with the N atom to which they are bonded, form a radical of a heterocycle from the group consisting of pyrrole, pyrrolidine, imidazole, pyrazole, piperidine, piperazine, morpholine, pyrazoline, imidazoline, thiomorpholine, thiazolidine, 1-oxothiomorpholine, 1,1-dioxothiomorpholine and hexamethyleneimine, where this heterocycle is unsubstituted or is mono-, di- or trisubstituted by
1. the radicals described under 3.1 to 3.11,
2. ($C_1$–$C_4$)-alkyl,
3. ($C_1$–$C_4$)-alkyl, which is substituted as described under 3.1 to 3.11, $R^3$ is hydrogen or methoxy, Ar is phenyl, which is mono-, di- or trisubstituted by
1. halogen,
2. —$NO_2$,
3. —O—($C_1$–$C_3$)-alkyl,
4. ($C_1$–$C_2$)-alkyl, which is unsubstituted or is mono-, di- or trisubstituted by halogen,
5. —C(O)—$NH_2$.

Particularly preferred compounds of the formula I and/or stereoisomeric forms of the compounds of the formula I and/or mixtures of such forms in all ratios and/or physiologically tolerable salts of the compounds of the formula I are those in which $R^1$ and $R^2$ are identical or different and independently of one another are
1. hydrogen,
2. ($C_1$–$C_3$)-alkyl,
3. ($C_1$–$C_3$)-alkyl, which is mono- or disubstituted by
   - 3.1 —OH
   - 3.2 —O—$CH_3$,
   - 3.3 —N($R^6$)$R^7$, in which $R^6$ and $R^7$ are identical or different and independently of one another are hydrogen or ($C_1$–$C_3$)-alkyl,
   - 3.4 —O—($C_1$–$C_2$)-alkyl which is mono- or disubstituted by —OH,
   - 3.5 a radical of a heterocycle from the group consisting of morpholine and pyridine,
- 4. ($C_5$–$C_6$)-cycloalkyl, which is unsubstituted or is substituted by
  - 4.1 ($C_1$–$C_4$)-alkyl,
  - 4.2 —OH,
  - 4.3 —O—($C_1$–$C_4$)-alkyl,
  - 4.4 —$NH_2$, or $R^1$ and $R^2$, together with the N atom to which they are bonded, form a piperazine radical which is unsubstituted or is substituted by
1. —$CH_2$-phenyl,
2. —$CH_2$—C(O)-morpholino,
3. —$CH_2$—C(O)—$NH_2$,
4. ($C_1$–$C_3$)-alkyl, which is monosubstituted by —OH,
5. methyl or ethyl,
6. —$CH_2$—C(O)—NH—CH($CH_3$)$_2$, $R^3$ is hydrogen or methoxy, Ar is phenyl, which is mono-, di- or trisubstituted by
1. halogen,
2. —$NO_2$,
3. —O—($C_1$–$C_3$)-alkyl,
4. ($C_1$–$C_2$)-alkyl, which is unsubstituted or is mono-, di- or trisubstituted by halogen,
5. —C(O)—$NH_2$.

Especially preferred compounds of the formula I and/or stereoisomeric forms of the compounds of the formula I and/or mixtures of such forms in all ratios and/or physiologically tolerable salts of the compounds of the formula I are those in which one or both of the radicals $R^1$ and $R^2$ are unsubstituted or substituted cycloalkyl radicals. For example, one of the radicals $R^1$ and $R^2$ can be an unsubstituted or substituted cycloalkyl radical and the other of the radicals $R^1$ and $R^2$ can have another meaning, for example hydrogen or alkyl, or both radicals $R^1$ and $R^2$ can be cycloalkyl. Preferred cycloalkyl radicals in compounds of this type are unsubstituted cycloalkyl radicals and substituted cycloalkyl radicals which carry one, two or three substituents, in particular one or two substituents. Preferred substituents in substituted cycloalkyl radicals of this type, are alkyl groups and hydroxyl groups, in particular hydroxyl groups. Very particularly preferred substituted cycloalkyl radicals are those cycloalkyl radicals which carry one hydroxyl group as a substituent. Cycloalkyl radicals in preferred compounds of the formula I of this type are preferably cyclopentyl radicals and cyclohexyl radicals. Especially preferred substituted cycloalkyl radicals in compounds of this type are hydroxycyclopentyl radicals and hydroxycyclohexyl radicals, for example the 4-hydroxycyclohexyl radical. Substituents in substituted cycloalkyl radicals, however, can be situated in any desired positions and can be present in any desired stereochemical arrangement and independently of one another are in the cis position or trans position.

A specific group of compounds according to the invention is formed by compounds of the formula I and/or stereoisomeric forms of the compounds of the formula I and/or physiologically tolerable salts of the compounds of the formula I, where $R^1$ and $R^2$ are identical or different and independently of one another are
1. a hydrogen atom,
2. ($C_1$–$C_5$)-alkyl,
3. ($C_1$–$C_5$)-alkyl, which is mono-, di- or trisubstituted by
   - 3.1 —OH
   - 3.2 —O—($C_1$–$C_6$)-alkyl,
   - 3.3 —SH, 3.5 —SR$^4$, in which R$^4$ is (C$_1$–C$_6$)-alkyl,
3.6 —NH$_2$
3.7 —N(R$^6$)R$^7$, in which R$^6$ and R$^7$ are identical or different and independently of one another are a hydrogen atom or (C$_1$–C$_6$)-alkyl,
3.8 —C(O)—NH$_2$
3.9 —C(O)—N(R$^6$)R$^7$, in which R$^6$ and R$^7$ are identical or different and independently of one another are a hydrogen atom or (C$_1$–C$_6$)-alkyl or R$^6$ and R$^7$, together with the N atom to which they are bonded, form a morpholine, piperazine, imidazole, piperidine, pyrrolidine, pyridine, thiomorpholine, 1-oxothiomorpholine, 1,1-dioxothiomorpholine or a hexamethyleneimine radical,
3.10 —O—(C$_1$–C$_6$)-alkyl, which is mono-, di- or trisubstituted by
   3.10.1 —OH,
   3.10.2 —SH,
   3.10.3 =O or
   3.10.4 —COOH,
3.11 —COOH,
3.12 —C(O)—O—R$^8$, in which R$^8$ is (C$_1$–C$_6$)-alkyl,
3.13 phenyl,
3.14 phenyl, in which the phenyl ring is mono-, di- or trisubstituted by
   3.14.1 —O—(C$_1$–C$_4$)-alkyl,
   3.14.2 —O-phenyl,
   3.14.3 (C$_1$–C$_4$)-alkyl,
   3.14.4 —NO$_2$,
   3.14.5 halogen or
   3.14.6 —C(R$^9$)(R$^{10}$)R$^{11}$, in which R$^9$, R$^{10}$ and R$^{11}$ independently of one another are a hydrogen atom or halogen,
3.15 a radical of a heterocycle from the group consisting of morpholine, piperazine, imidazole, piperidine, pyrrolidine, pyridine, thiomorpholine, 1-oxothiomorpholine, 1,1-dioxothiomorpholine, hexamethyleneimine, pyrrole, pyrazole, pyridazine, pyrazine, pyrimidine, indolizine, indole, indazole, purine, quinoxaline, furan, quinazoline, cinnoline, pteridine, oxazole, isoxazole, thiazole, isothiazole, furazan, indoline, pyrazoline, thiophene, xanthine, imidazoline or pyran, or
3.16 a radical of a heterocycle as described in 3.15, which is mono-, di-, tri- or tetrasubstituted by
   3.16.1 (C$_1$–C$_4$)-alkyl,
   3.16.2 =O,
   3.16.3 halogen,
   3.16.4 —O—(C$_1$–C$_4$)-alkyl or
   3.16.5 —NO$_2$,
4. (C$_3$–C$_7$)-cycloalkyl or
5. a radical of a heterocycle from the group consisting of morpholine, piperazine, imidazole, piperidine, pyrrolidine, pyridine, thiomorpholine, 1-oxothiomorpholine, purine, 1,1-dioxothiomorpholine, hexamethyleneimine, pyrrole, pyrazole, pyrazine, pyrimidine, pyridazine, indolizine, indole, indazole, quinoxaline, quinazoline, cinnoline, pteridine, oxazole, isoxazole, thiazole, isothiazole, furan, furazan, indoline, pyrazoline, thiophene, xanthine, imidazoline or pyran, where this heterocyclic radical is unsubstituted or is substituted by
1. the radicals described under 3.1 to 3.16,
2. (C$_1$–C$_6$)-alkyl or
3. (C$_1$–C$_6$)-alkyl, which is substituted as described under 3.1 to 3.16, or R$^1$ and R$^2$, together with the N atom to which they are bonded, form a radical of a heterocycle from the group consisting of pyrrole, pyrrolidine, imidazole, pyrazole, piperidine, piperazine, morpholine, pyrazoline, imidazoline, thiomorpholine, thiazolidine, 1-oxothiomorpholine, 1,1-dioxothiomorpholine and hexamethyleneimine, where this heterocyclic radical is unsubstituted or is substituted by
1. the radicals described under 3.1 to 3.16,
2. (C$_1$–C$_6$)-alkyl or
3. (C$_1$–C$_6$)-alkyl, which is substituted as described under 3.1 to 3.16, R$^3$ is a hydrogen atom or methoxy and
Ar is phenyl which is mono-, di- or trisubstituted by
1. halogen,
2. —NO$_2$,
3. —O—(C$_1$–C$_6$)-alkyl,
4. —(C$_1$–C$_6$)-alkyl, which is unsubstituted or is mono-, di- or trisubstituted by halogen,
5. —C(O)—NH$_2$ or
6. —C(O)—N(R$^{12}$)R$^{13}$, in which R$^{12}$ and R$^{13}$ are identical or different and independently of one another are a hydrogen atom or (C$_1$–C$_6$)-alkyl.

Examples of substituted phenyl radicals which can be Ar are halophenyl radicals, for example chlorophenyl radicals such as 3-chlorophenyl or 4-chlorophenyl, alkylphenyl radicals, for example methylphenyl radicals such as 3-methylphenyl or 4-methylphenyl, or trifluoromethylphenyl radicals, for example 4-trifluoromethylphenyl or 3,5-bistrifluoromethylphenyl. A subgroup of compounds of the formula I is formed from those compounds in which the phenyl radical which is Ar only carries one substituent, for example a substituent which is selected from the group consisting of halogen and (C$_1$–C$_4$)-alkyl. A second subgroup is formed from those compounds of the formula I in which the phenyl radical which is Ar carries two or three identical or different substituents. A further subgroup is formed from those compounds in which a hydroxyl group is present in the radicals R$^1$ and/or R$^2$. An example of the group —N(R$^6$)R$^7$ is the group —NH$_2$; an example of the groups —C(O)—N(R$^6$)R$^7$ and —C(O)—N(R$^{12}$)R$^{13}$ is the group —C(O)—NH$_2$.

If groups in compounds of the formula I can be substituted by a number of substituents, in all cases the substituents can all be identical or can in some cases be identical or can all be different. This applies to the substituents which are specifically mentioned as possible substituents of a group in the definition of the compounds of the formula I, and also applies if several substituents of the same type are present in a group, for example several halogen atoms and/or several (C$_1$–C$_4$)-alkyl radicals, which latter radicals can then be, for example, methyl groups and/or ethyl groups and/or butyl groups. If the resulting group or the molecule of the formula I is stable and has no undesired properties on account of the substitution concerned, substituents can occur in any desired combinations and can be situated in any desired positions in a group. Compounds of the formula I according to the invention in general, however, contain not more than two nitro groups in the molecule.

Alkyl radicals can be straight-chain or branched. This also applies if they are substituted, for example by a phenyl radical or by hydroxyl, or if they are contained in other groups, for example in alkoxy groups. Examples of alkyl groups are methyl, ethyl, n-propyl, isopropyl, n-butyl, isobutyl, sec-butyl, tert-butyl, n-pentyl, isopentyl, neopentyl, n-hexyl, 3,3-dimethylbutyl, n-heptyl, n-octyl. The term alkyl is to be understood here as also meaning unsaturated alkyl radicals, in particular alkyl radicals which contain one or two double bonds or one or two triple bonds or one double bond and one triple bond. Examples of such radicals are the vinyl radical, the 2-propenyl radical (allyl radical), the 2-butenyl radical, the 3-methyl-2-butenyl radical, the ethynyl radical, the 2-propynyl radical (propargyl radical) or the 3-butynyl radical.

Examples of cycloalkyl are cyclopropyl, cyclobutyl, cyclopentyl, cyclohexyl or cycloheptyl. Substituted cycloalkyl radicals are preferably substituted by one, two, three or four identical or different substituents, particularly preferably by one or two identical or different substituents.

Halogen is fluorine, chlorine, bromine or iodine, preferably fluorine or chlorine.

In monosubstituted phenyl radicals, the substituent can be situated in the 2 position, the 3 position or the 4 position. If phenyl is disubstituted, the substituents can be situated in the 2,3 position, the 2,4 position, the 2,5 position, the 2,6 position, the 3,4 position or the 3,5 position. In trisubstituted phenyl radicals, the substituents can be situated in the 2,3,4 position, the 2,3,5 position, the 2,4,5 position, the 2,4,6 position, the 2,3,6 position or the 3,4,5 position.

Heterocyclic radicals can be bonded via all suitable atoms, both via carbon atoms and via nitrogen atoms, if this is in accord with the respective definition of the substituent. For example, a piperidine radical can be a 1-piperidinyl radical (=piperidino radical), a 2-piperidinyl radical, a 3-piperidinyl radical or a 4-piperidinyl radical. Imidazolyl can be 1-imidazolyl, 2-imidazolyl, 4-imidazolyl or 5-imidazolyl; pyridyl can be 2-pyridyl, 3-pyridyl or 4-pyridyl.

In the case of appropriate substitution, the compounds of the formula I can be present in stereoisomeric forms or in mixtures of stereoisomeric forms. If the compounds of the formula I contain one or more asymmetric centers, these can independently of one another have the S configuration or the R configuration. The invention includes all possible stereoisomers, for example enantiomers and diastereomers, and mixtures of two or more stereoisomeric forms, for example mixtures of enantiomers and/or diastereomers, in all ratios. The invention thus relates to enantiomers in enantiomerically pure form, both as levorotatory and as dextrorotatory antipodes, in the form of racemates and in the form of mixtures of the two enantiomers in all ratios. In the presence of cis/trans isomerism, the invention relates both to the cis form and the trans form and mixtures of these forms in all ratios. The individual stereoisomers can, if desired, be prepared by resolution of a mixture according to customary methods, for example by chromatography or crystallization, by the use of stereochemically homogeneous starting substances in the synthesis or by stereoselective synthesis. If appropriate, derivatization can be carried out before separation of stereoisomers. A stereoisomer mixture can be separated at the stage of the compounds of the formula I or at the stage of a starting substance or of an intermediate in the course of the synthesis. In the presence of tautomeric forms, the invention also includes all possible tautomers.

If the compounds of the formula I contain one or more acidic or basic groups, the invention also relates to the corresponding physiologically or toxicologically tolerable salts, in particular the pharmaceutically utilizable salts. Thus the compounds of the formula I which contain one or more acidic groups, for example COOH groups in phenyl rings or acidic hydroxyl groups, on these groups can be present and can be used according to the invention, for example, as alkali metal salts, alkaline earth metal salts or ammonium salts. Examples of such salts are sodium salts, potassium salts, calcium salts, magnesium salts or salts with ammonia or organic amines such as, for example, ethylamine, ethanolamine, triethanolamine or amino acids. Compounds of the formula I which contain one or more basic, that is protonatable, groups, can be present in the form of their acid addition salts with inorganic or organic acids and can be used according to the invention, for example, as salts with hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid etc. If the compounds of the formula I simultaneously contain acidic and basic groups in the molecule, in addition to the salt forms described, the invention also includes internal salts or betaines. Salts can be obtained from the compounds of the formula I by customary processes known to the person skilled in the art, for example by combination with an organic or inorganic acid or base in a solvent or dispersant, or else from other salts by anion exchange or cation exchange. The present invention also includes all salts of the compounds of the formula I which, because of lower physiological tolerability, are not directly suitable for use in pharmaceuticals, but are suitable, for example, as intermediates for chemical reactions or for the production of physiologically tolerable salts.

The present invention furthermore includes all solvates of compounds of the formula I, for example hydrates or adducts with alcohols, and also derivatives of the compounds of the formula I, for example esters, prodrugs and active metabolites.

The invention furthermore relates to processes for the preparation of the compounds of the formula I. Starting materials for a process for the preparation of compounds of the formula I are o-aminobenzamides or o-aminobenzoic acid esters of the formula II, in which X can be, for example, amino or —O—($C_1$–$C_4$)-alkyl. The compounds of the formula II can be reacted with benzoic acids or their activated derivatives, for example the benzoyl chlorides of the formula III, to give the compounds of the formula IV. The compounds of the formula IV, can then be reacted to give the 4-hydroxyquinazolines of the formula V which, for example, can be reacted by chlorination with chlorinating agents to give compounds of the formula VI. From the compounds of the formula VI and the desired amines of the formula HN($R^1$)$R^2$, the compounds of the formula I can then be obtained by replacement of the chlorine atom by the amino group. Suitable solvents for this replacement reaction are, for example, water, alcohols, tetrahydrofuran (THF), dioxane, dimethylformamide (DMF), N-methylpyrrolidone (NMP), benzene, toluene, xylene, chlorobenzene and dichlorobenzene.

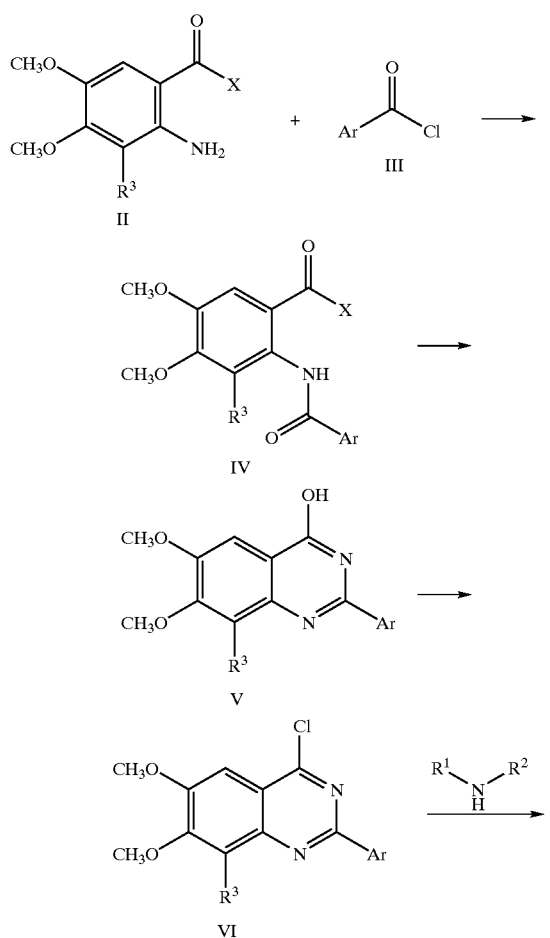

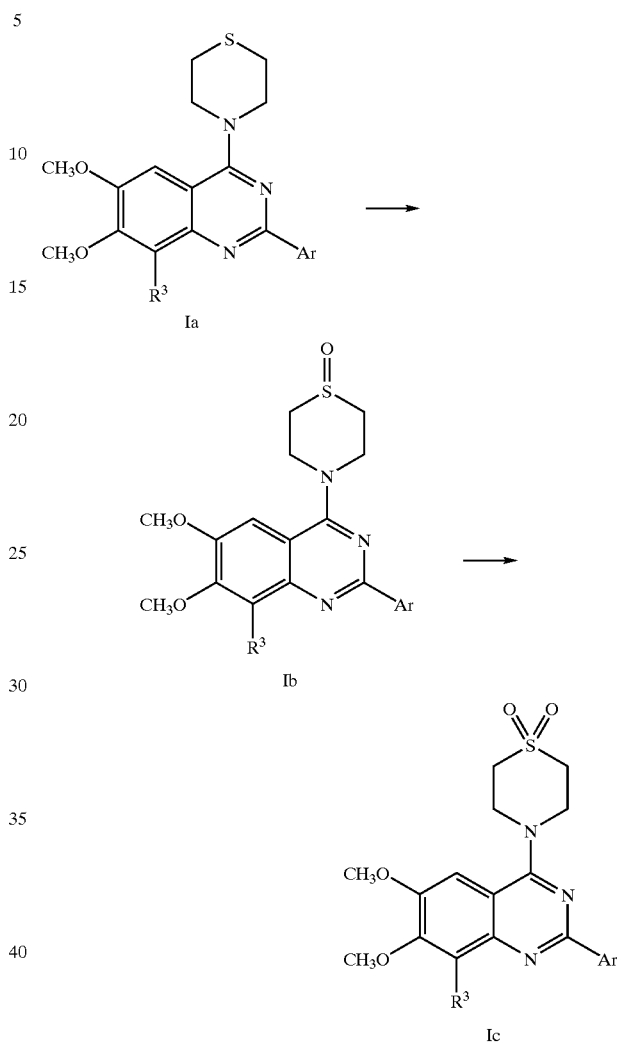

example using hydrogen peroxide in glacial acetic acid, to the corresponding sulfoxides and sulfones, for example the compounds of the formula Ia to the compounds of the formula Ib and the compounds of the formula Ic.

The chlorination of the compounds of the formula V to give the compounds of the formula VI can advantageously be carried out, for example, using phosphorus chlorides such as phosphorus oxychloride and/or phosphorus pentachloride or using other chlorinating agents. The cyclization to the compounds of the formula V can be brought about by acids and particularly advantageously using bases. In the case of compounds of the formulae II and IV, in which X is Oalkyl, ammonia is needed for the cyclization. The reaction can then be advantageously carried out at elevated pressure. The acylation of the amino compounds of the formula II with the arylcarboxylic acid derivatives such as the acid chlorides of the formula III can be carried out by known variants of amide preparation.

These reactions can be carried out in a wide temperature range. Reaction temperatures of 20 to 150° C. are preferred. The reactions in the first, second and last step can be accelerated by bases such as sodium bicarbonate, sodium carbonate, potassium carbonate, triethylamine, sodium alkoxides or pyridine and in the last step additionally by excess amine. The intermediates and the final compounds of the formula I can be separated off from the reaction mixtures and purified by customary processes such as crystallization, sublimation or chromatography, for example column chromatography. The starting compounds of the formulae II and III and also the amines of the formula $R^1(R^2)NH$ are commercially obtainable or described in the literature or can be prepared according to known standard reactions.

Compounds of the formula I which contain a thiomorpholino group can be oxidized by known methods, for Depending on the functional groups which are contained in the starting compounds for the synthesis of the compounds of the formula I or which should be contained in the final compounds of the formula I, and depending on the synthesis process used, it may be appropriate for the avoidance of undesired reactions or side reactions to use protective group techniques in certain synthesis steps. Instead of temporarily blocking functional groups by suitable protective groups, however, they can initially also be present in the form of precursors which are then later converted into the desired group, for example amino groups in the form of nitro groups or cyano groups.

The compounds of the formula I according to the invention bring about, via the activation of the soluble guanylate cyclase (sGC), an increase in the cGMP concentration and are therefore valuable agents for the therapy and prophylaxis of diseases which are associated with a low or lowered cGMP level or are caused by such a level or for whose therapy or prophylaxis an increase in the cGMP level present is desired. The activation of the sGC by the compounds of the formula I can be investigated, for example, in the activity assay described below.

Diseases and pathological conditions which are associated with a low cGMP level or in which an increase in the cGMP level is desired and for whose therapy and prophylaxis compounds of the formula I can be employed are, for example, cardiovascular conditions such as endothelial dysfunction, diastolic dysfunction, atherosclerosis, high blood pressure, stable and unstable angina pectoris, thromboses, restenoses, myocardial infarcts, strokes, cardiac insufficiency or pulmonary hypertension, or, for example, erectile dysfunction, bronchial asthma, chronic renal insufficiency and diabetes. Compounds of the formula I can moreover be employed in the therapy of cirrhosis of the liver and also for improving restricted learning ability or memory power.

The compounds of the formula I and their physiologically tolerable salts and also other physiological tolerable derivatives, for example prodrugs, can thus be used in animals, preferably in mammals, and in particular in humans as pharmaceuticals on their own, in mixtures with one another or in the form of pharmaceutical preparations. The present invention therefore also relates to the compounds of the formula I and their physiologically tolerable salts and derivatives for use as pharmaceuticals, their use for the normalization of a disturbed cGMP balance and in particular their use in the therapy and prophylaxis of the abovementioned syndromes, and also their use for the production of medicaments for these. The present invention furthermore relates to the use of the compounds, already known as such, 2-(p-chlorophenyl)-4-((1-diethylamino-4-pentyl)amino)-6,7-dimethoxyquinazoline dihydrochloride and 2-(p-chlorophenyl-4-(4-hydroxybutyl)amino-6,7,8-trimethoxyquinazoline for use as pharmaceuticals, their use for the activation of the soluble guanylate cyclase and for the normalization of a disturbed cGMP balance, their use in the therapy and prophylaxis of the abovementioned syndromes, and also their use for the production of medicaments for these.

The present invention also relates to pharmaceuticals and pharmaceutical 5 preparations which comprise an efficacious amount of at least one compound of the formula I and/or of a physiologically tolerable salt thereof and/or of another physiologically tolerable derivative thereof, for example of a prodrug, together with a pharmaceutically suitable and physiologically tolerable carrier. The pharmaceutical preparations normally contain 0.2 to 500 mg, preferably 1 to 200 mg, of active compound of the formula I and/or its physiologically tolerable salts and/or derivatives per dose.

The pharmaceuticals can be administered orally, for example in the form of pills, tablets, film-coated tablets, sugar-coated tablets, granules, hard and soft gelatin capsules, aqueous, alcoholic or oily solutions, syrups, emulsions or suspensions, or rectally, for example in the form of suppositories. The administration, however, can also be carried out parenterally, for example subcutaneously, intramuscularly or intravenously in the form of injection solutions or infusion solutions. Further suitable administration forms are, for example, percutaneous or topical application, for example in the form of ointments, tinctures, sprays or transdermal therapeutic systems, or administration by inhalation in the form of nasal sprays or aerosol mixtures, or, for example, microcapsules, implants or rods. The preferred administration form depends, for example, on the disease to be treated and its severity.

The pharmaceutical preparations normally contain 0.5 to 90 percent by weight of the compounds of the formula I and/or their physiologically tolerable salts and/or derivatives. The pharmaceutical preparations can be prepared in a manner known per se. For this, one or more compounds of the formula I and/or their physiologically tolerable salts and/or derivatives are brought, together with one or more solid or liquid pharmaceutical vehicles and/or excipients and, if desired, in combination with other pharmaceutical active compounds having therapeutic or prophylactic action, into a suitable administration form or dosage form which can then be used as a pharmaceutical in human medicine or veterinary medicine.

For the production, for example, of pills, tablets, sugar-coated tablets and hard gelatin capsules, it is possible to use lactose, starch, for example cornstarch, or starch derivatives, talc, stearic acid or its salts. Vehicles for soft gelatin capsules and suppositories are, for example, fats, waxes, semisolid and liquid polyols, natural or hardened oils. Suitable vehicles for the production of solutions, for example injection solutions, or of emulsions or syrups are, for example, water, physiological saline solution, alcohols such as ethanol, glycerol, polyols, sucrose, invert sugar, glucose, mannitol, vegetable oils. The compounds of the formula I and their physiologically tolerable salts can also be lyophilized and the lyophilizates obtained used, for example, for the production of injection or infusion preparations. Suitable vehicles for microcapsules, implants or rods are, for example, copolymers of glycolic acid and lactic acid.

In addition to the active compounds and vehicles, the pharmaceutical preparations can additionally contain customary additives, for example fillers, disintegrants, binders, lubricants, wetting agents, stabilizers, emulsifiers, dispersants, preservatives, sweeteners, colorants, flavorings or aromatizers, thickening agents, diluents, buffer substances, furthermore solvents or solubilizers or agents for achieving a depot effect, salts for changing the osmotic pressure, coating agents or antioxidants. They can furthermore contain one or more other pharmaceutical active compounds.

The dosage of the active compound of the formula I and/or of a physiologically tolerable salt and/or derivative thereof to be administered depends on the individual case and is to be tailored to the individual conditions as is customary for an optimal action. Thus it depends on the nature and severity of the disease to be treated and on sex, age, weight and individual responsiveness of the human or animal to be treated, on the potency and duration of action of the compounds employed, on whether treatment is acute or chronic or prophylaxis is conducted, or on whether further active compounds are administered in addition to compounds of the formula I. In general, a daily dose of approximately 0.01. to 100 mg/kg, preferably 0.1 to 10 mg/kg, in particular 0.3 to 5 mg/kg (in each case mg per kg of body weight), is appropriate to achieve effective results in the case of administration to an adult weighing about 75 kg. The daily dose can be administered in one individual dose or, in particular in the case of the administration of relatively large amounts, can be divided into a number of, for example two, three or four, individual doses. If appropriate, depending on individual behavior, it may be necessary to deviate upwards or downwards from the daily dose indicated.

The compounds of the formula I activate the soluble guanylate cyclase. On account of this property, apart from being used as pharmaceutical active compounds in human medicine and veterinary medicine, they can also be used as a scientific tool or as an aid for biochemical investigations in which influencing of the guanylate cyclase of this type is intended, and for diagnostic purposes, for example in the in vitro diagnosis of cell samples or tissue samples. Furthermore, the compounds of the formula I and their salts can be used as intermediates for the production of further pharmaceutical active compounds, which are obtainable, for example, from the compounds of the formula I by modifications of functional groups or introduction of substituents.

The following examples illustrate the invention without restricting it.

EXAMPLE 1

Methyl 2-(4-Chlorobenzoylamino)-3,4,5-trimethoxybenzoate (Intermediate)

A solution of 20.3 g of 4-chlorobenzoyl chloride in 60 ml of THF was added dropwise to the solution of 25.3 g of methyl 2-amino-3,4,5-trimethoxybenzoate and 16 ml of triethylamine in 100 ml of THF. The mixture was refluxed for 1 hour (h), cooled in an ice bath and filtered. After concentration, a colorless residue remained. Yield: 34.1 g. Melting point (m.p.): 116° C.

EXAMPLE 2

2-(4-Chlorophenyl)-4-hydroxy-6,7,8-trimethoxyquinazoline (Intermediate)

A suspension of 28.5 g of methyl 2-(4-chlorobenzoylamino)-3,4,5-trimethoxybenzoate in 200 ml of methanol was treated with 150 ml of liquid ammonia and heated at 100° C. for 5 h in an autoclave. On cooling, a precipitate deposited, which was filtered off with suction and dried under reduced pressure. Yield: 25 g. M.p.: 289° C.

EXAMPLE 3

2-(4-Chlorophenyl)-4-chloro-6,7,8-trimethoxyquinazoline (Intermediate)

18.2 g of 2-(4-chlorophenyl)-hydroxy-6,7,8-trimethoxyquinazoline were heated at 100° C. for 3 h in 120 ml of phosphorus oxychloride. The excess phosphorus oxychloride was distilled off and the oily residue was stirred with ice water. The solid was filtered off with suction and dried under reduced pressure. Yield: 15.0 g. M.p.: 159° C.

EXAMPLE 4

2-Nitro-4,5-dimethoxybenzamide (Intermediate)

A mixture of 45.5 g of 2-nitro-4,5-dimethoxybenzoic acid and 120 ml of thionyl chloride was heated at 80° C. until a clear solution was formed. The excess thionyl chloride was distilled off, the residue was treated with toluene and the mixture was n conentrated again. The oily residue was added dropwise to 300 ml of concentrated aqueous ammonia solution. After stirring briefly, the precipitate was filtered off with suction and dried under reduced pressure. Yield: 29 g. M.p.: 201° C.

EXAMPLE 5

2-Amino-4,5-dimethoxybenzamide (Intermediate)

A suspension of 28 g of 2-nitro-4,5-dimethoxybenzamide was hydrogenated under normal pressure in the presence of 1.5 g of platinum dioxide hydrate until hydrogen was no longer absorbed. The catalyst was filtered off with suction, the filtrate was evaporated and the residue was dried under reduced pressure. Yield: 24.1 g. M.p.: 147° C.

EXAMPLE 6

2-(4-Chlorobenzoylamino)-4,5-dimethoxybenzamide (Intermediate)

A mixture of 13.7 g of 2-amino-4,5-dimethoxybenzamide, 8.1 g of triethylamine, 13.8 g of 4-chlorobenzoyl chloride and 300 ml of methylene. chloride was stirred for 2 h without cooling. The precipitate was filtered off with suction, stirred with water, filtered off with suction and dried under reduced pressure. Yield: 22.5 g. M.p.: 243° C.

EXAMPLE 7

2-(4-Chlorophenyl)-4-hydroxy-6,7-dimethoxyquinazoline (Intermediate)

21.3 g of 2-(4-chlorobenzoylamino)-4,5-dimethoxybenzamide were heated at 100° C. for 2 h in 250 ml of 10% strength sodium hydroxide solution. The starting compound gradually went into solution in the course of this and a little later a precipitate deposited again. The mixture was diluted with 500 ml of water and adjusted to pH=4 using concentrated hydrochloric acid. After stirring for a further 2 h, the solid was filtered off with suction, washed with plenty of water and dried at 40° C. under reduced pressure. Yield: 19.0 g. M.p.: 329° C.

EXAMPLE 8

2-(4-Chlorophenyl)-4-chloro-6,7-dimethoxyquinazoline (Intermediate)

The preparation was carried out analogously to Example 3. M.p.: 290° C.

EXAMPLE 9

2-(4-Chlorophenyl)-4-(4-benzylpiperazino)-6,7,8-trimethoxyquinazoline

A mixture of 2.0 g of 2-(4-chlorophenyl)-4-chloro-6,7,8-trimethoxyquinazoline and 5.0 g of N-benzylpiperazine was heated at 150° C. for 1 h. After cooling, 20 ml of ice water were added and the mixture was extracted with ethyl acetate. The organic phase was dried over sodium sulfate and concentrated. The oily crude product thus obtained was recrystallized from isopropanol. Yield: 1 g. M.p.: 150° C.

The following compounds were prepared analogously.

EXAMPLE 10

2-(4-Chlorophenyl)-4-(4-(2-methoxyphenyl)piperazino)-6,7,8-trimethoxyquinazoline M.p.: 157° C.

EXAMPLE 11

2-(4-Chlorophenyl)-4-(2-diisopropylaminoethylamino)-6,7,8-trimethoxyquinazoline Hydrochloride M.p.: 189° C.

EXAMPLE 12

2-(4-Chlorophenyl)-4-(4-(morpholinocarbonylmethyl)piperazino)-6,7,8-trimethoxyquinazoline M.p.: 177° C.

EXAMPLE 13

2-(4-Chlorophenyl)-4-(4-(2-hydroxyethyl)piperazino)-6,7,8-trimethoxyquinazoline

M.p.: 175° C.

EXAMPLE 14

2-(4-Chlorophenyl)-4-(3-morpholinopropylamino)-6,7,8-trimethoxyquinazoline Hydrochloride M.p.: 190° C.

EXAMPLE 15

2-(4-Trifluoromethylphenyl)-4-hydroxy-6,7-dimethoxyquinazoline (Intermediate)

M.p.: 338° C.

EXAMPLE 16

2-(4-Trifluoromethylphenyl)-4-chloro-6,7-dimethoxyquinazoline (Intermediate)

M.p.: 181° C.

EXAMPLE 17

2-(4-Chlorophenyl)-4-(4-methylpiperazino)-6,7-dimethoxyquinazoline Hydrochloride M.p.: 249° C.

EXAMPLE 18

2-(4-Chlorophenyl)-4-(2-diisopropylaminoethylamino)-6,7-dimethoxyquinazoline Dihydrochloride M.p.: 246° C.

EXAMPLE 19

2-(4-Chlorophenyl)-4-(4-benzylpiperazino)-6,7-dimethoxyquinazoline Dihydrochloride M.p.: 225° C.

EXAMPLE 20

2-(4-Chlorophenyl)-4-(2-hydroxyethylamino)-6,7-dimethoxyquinazoline

M.p.: 236° C.

EXAMPLE 21

2-(4-Chlorophenyl)-4-(3-(1-imidazolyl)propylamino)-6,7-dimethoxyquinazoline

M.p.: 242° C.

EXAMPLE 22

2-(4-Chlorophenyl)-4-((1-benzylpiperidin-4-yl)amino)-6,7-dimethoxyquinazoline

M.p.: 252° C.

EXAMPLE 23

2-(4-Chlorophenyl)-4-(4-(2-hydroxyethyl)piperazino)-6,7-dimethoxyquinazoline

M.p.: 163° C.

EXAMPLE 24

2-(4-Chlorophenyl)-4-(4-(isopropylaminocarbonylmethyl)piperazino)-6,7-dimethoxyquinazoline M.p.: 187° C.

EXAMPLE 25

2-(4-Chlorophenyl)-4-((aminocarbonylmethyl)amino)-6,7-dimethoxyquinazoline

M.p.: 291° C.

EXAMPLE 26

2-(4-Chlorophenyl)-4-((2,2,6,6-tetramethylpiperidin-4-yl)amino)-6,7-dimethoxyquinazoline M.p.: 231° C.

EXAMPLE 27

2-(4-Chlorophenyl)-4-(3-(2-oxopyrrolidino)propylamino)-6,7-dimethoxyquinazoline

M.p.: 210° C.

EXAMPLE 28

2-(4-Chlorophenyl)-4-((3-pyridylmethyl)amino)-6,7-dimethoxyquinazoline

M.p.: 232° C.

EXAMPLE 29

2-(4-Methylphenyl)-4-hydroxy-6,7-dimethoxyquinazoline (Intermediate)

M.p.: 305° C.

EXAMPLE 30

2-(4-Chlorophenyl)-4-(4-(morpholinocarbonylmethyl)piperazino)-6,7-dimethoxyquinazoline M.p.: 198° C.

EXAMPLE 31

2-(4-Methylphenyl)-4-chloro-6,7-dimethoxyquinazoline (Intermediate)

M.p.: 289° C.

EXAMPLE 32

2-(4-Chlorophenyl)-4-(3-hydroxypropylamino)-6,7-dimethoxyquinazoline

M.p.: 187° C.

EXAMPLE 33

2-(4-Chlorophenyl)-4-(2-(2-hydroxyethoxy)ethylamino)-6,7-dimethoxyquinazoline

M.p.: 188° C.

EXAMPLE 34

N-(2-(4-Chlorophenyl)-6,7-dimethoxyquinazolin-4-yl)aminoacetic Acid

M.p.: 270° C. (dec.)

EXAMPLE 35

2-(4-Chlorophenyl)-4-dimethylamino-6,7-dimethoxyquinazoline

M.p.: 148° C.

EXAMPLE 36

2-(4-Chlorophenyl)-4-(2-methoxyethylamino)-6,7-dimethoxyquinazoline

M.p.: 178° C.

EXAMPLE 37

2-(4-Methylphenyl)-4-(2-hydroxyethylamino)-6,7-dimethoxyquinazoline

M.p.: 217° C.

EXAMPLE 38

2-(4-Methylphenyl)-4-((3-pyridylmethyl)amino)-6,7-dimethoxyquinazoline

M.p.: 239° C.

EXAMPLE 39

2-(4-Methylphenyl)-4-(4-methylpiperazino)-6,7-dimethoxyquinazoline

M.p.: 166° C.

EXAMPLE 40

2-(4-Methylphenyl)-4-(2-diisopropylaminoethylamino)-6,7-dimethoxyquinazoline

M.p.: 81° C.

EXAMPLE 41

2-(4-Chlorophenyl)-4-(N-(2-hydroxyethyl)-N-methylamino)-6,7-dimethoxyquinazoline M.p.: 129° C.

EXAMPLE 42

2-(4-Trifluoromethylphenyl)-4-(2-hydroxyethylamino)-6,7-dimethoxyquinazoline

M.p.: 210° C.

EXAMPLE 43

2-(4-Trifluoromethylphenyl)-4-(4-(2-hydroxyethyl)piperazino)-6,7-dimethoxyquinazoline M.p.: 176° C.

EXAMPLE 44

2-(4-Trifluoromethylphenyl)-4-((3-pyridylmethyl)amino)-6,7-dimethoxyquinazoline

M.p.: 238° C.

EXAMPLE 45

2-(4-Trifluoromethylphenyl)-4-(4-methylpiperazino)-6,7-dimethoxyquinazoline

M.p.: 139° C.

EXAMPLE 46

2-(4-Chlorophenyl)-4-(2-(4-phenoxyphenyl)ethylamino)-6,7-dimethoxyquinazoline

M.p.: 216° C.

EXAMPLE 47

2-(4-Chlorophenyl)-4-((methoxycarbonylmethyl)amino)-6,7-dimethoxyquinazoline

M.p.: 196° C.

EXAMPLE 48

2-(4-Chlorophenyl)-4-morpholino-6,7-dimethoxyquinazoline

M.p.: 178° C.

EXAMPLE 49

2-(4-Methylphenyl)-4-morpholino-6,7-dimethoxyquinazoline

M.p.: 200° C.

EXAMPLE 50

2-(4-Trifluoromethylphenyl)-4-morpholino-6,7-dimethoxyquinazoline

M.p.: 207° C.

EXAMPLE 51

2-(4-Methylphenyl)-4-((4-pyridylmethyl)amino)-6,7-dimethoxyquinazoline

M.p.: 208° C.

EXAMPLE 52

2-(4-Methyl phenyl)-4-((2-pyridylmethyl)amino)-6,7-dimethoxyquinazoline

M.p.: 196° C.

EXAMPLE 53

2-(4-Methylphenyl)-4-((2-(2-pyridyl)ethyl)amino)-6,7-dimethoxyquinazoline

M.p.: 204° C.

EXAMPLE 54

2-(4-Chlorophenyl)-4-((3-pyridylmethyl)amino)-6,7,8-trimethoxyquinazoline

M.p.: 262° C.

EXAMPLE 55

2-(4-Chlorophenyl)-4-morpholino-6,7,8-trimethoxyquinazoline

M.p.: 153° C.

EXAMPLE 56

2-(4-Chlorophenyl)-4-piperazino-6,7,8-trimethoxyquinazoline

M.p.: 156° C.

EXAMPLE 57

2-(4-Chlorophenyl)-4-(2-hydroxyethylamino)-6,7,8-trimethoxyquinazoline

M.p.: 202° C.

EXAMPLE 58

2-(4-Chlorophenyl)-4-(2-methoxyethylamino)-6,7,8-trimethoxyquinazoline

M.p.: 165° C.

EXAMPLE 59

2-(4-Chlorophenyl)-4-(3-(1-imidazolyl) propylamino)-6,7,8-trimethoxyquinazoline

M.p.: 245° C.

EXAMPLE 60

2-(3,5-Bistrifluoromethylphenyl)-4-hydroxy-6,7,8-trimethoxyquinazoline (Intermediate)

M.p.: 335° C.

EXAMPLE 61

2-(3,5-Bistrifluoromethylphenyl)-4-chloro-6,7,8-trimethoxyquinazoline (Intermediate)

M.p.: 163° C.

EXAMPLE 62

2-(3,5-Bistrifluoromethylphenyl)-4-(4-methylpiperazino)-6,7,8-trimethoxyquinazoline M.p.: 176° C.

EXAMPLE 63

2-(3,5-Bistrifluoromethylphenyl)-4-(2-diisopropylaminoethylamino)-6,7,8-trimethoxyquinazoline M.p.: 128° C.

EXAMPLE 64

2-(3,5-Bistrifluoromethylphenyl)-4-morpholino-6,7,8-trimethoxyquinazoline

M.p.: 170° C.

EXAMPLE 65

2-(3,5-Bistrifluoromethylphenyl)-4-((3-pyridylmethyl)amino)-6,7,8-trimethoxyquinazoline M.p.: 229° C.

EXAMPLE 66

2-(4-Chlorophenyl)-4-thiomorpholino-6,7,8-trimethoxyquinazoline

M.p.: 174° C.

EXAMPLE 67

2-(4-Chlorophenyl)-4-(4-aminocarbonylpiperidino)-6,7,8-trimethoxyquinazoline

M.p.: 215° C.

EXAMPLE 68

2-(4-Chlorophenyl)-4-(1-oxothiomorpholino)-6,7,8-trimethoxyquinazoline

M.p.: 198° C.

EXAMPLE 69

2-(4-Chlorophenyl)-4-(1,1-dioxothiomorpholino)-6,7,8-trimethoxyquinazoline

M.p.: 241° C.

EXAMPLE 70

2-(4-Methylphenyl)-4-((3-methoxyphenylmethyl) amino)-6,7-dimethoxyquinazoline Hydrochloride M.p.: 278° C.

EXAMPLE 71

2-(4-Methylphenyl)-4-(2-(3-methoxyphenyl) ethylamino)-6,7-dimethoxyquinazoline Hydrochloride M.p.: 256° C.

EXAMPLE 72

2-(4-Methylphenyl)-4-((3-nitrophenylmethyl) amino)-6,7-dimethoxyquinazoline

M.p.: 250° C.

EXAMPLE 73

2-(4-Methylphenyl)-4-(2-(2-methoxyphenyl) ethylamino)-6,7-dimethoxyquinazoline

M.p.: 205° C.

EXAMPLE 74

2-(4-Chlorophenyl)-4-thiomorpholino-6,7-dimethoxyquinazoline

M.p.: 214° C.

EXAMPLE 75

2-(4-Methylphenyl)-4-thiomorpholino-6,7-dimethoxyquinazoline

M.p.: 213° C.

EXAMPLE 76

2-(4-Chlorophenyl)-4-(1-oxothiomorpholino)-6,7-dimethoxyquinazoline

M.p.: 226° C.

EXAMPLE 77

2-(4-Methylphenyl)-4-(1-oxothiomorpholino)-6,7-dimethoxyquinazoline

M.p.: 216° C.

EXAMPLE 78

2-(4-Chlorophenyl)-4-(4-(2-pyridyl)piperazino)-6,7,8-trimethoxyquinazoline

M.p.: 141° C.

EXAMPLE 79

2-(4-Methylphenyl)-4-(4-(2-pyridyl)piperazino)-6,7-dimethoxyquinazoline

M.p.: 191° C.

EXAMPLE 80

2-(4-Chlorophenyl)-4-dipropylamino-6,7,8-trimethoxyquinazoline

M.p.: 109° C.

EXAMPLE 81

2-(4-Chlorophenyl)-4-dipropylamino-6,7-dimethoxyquinazoline

M.p.: 223° C.

EXAMPLE 82

2-(3,5-Bistrifluoromethylphenyl)-4-dipropylamino-6,7,8-trimethoxyquinazoline

M.p.: 121° C.

EXAMPLE 83

2-(4-Methylphenyl)-4-(2,6-dimethylmorpholino)-6,7-dimethoxyquinazoline (cis/trans Mixture)

M.p.: 177° C.

EXAMPLE 84

2-(4-Methylphenyl)-4-(3-methoxypropylamino)-6,7-dimethoxyquinazoline

M.p.: 162° C.

EXAMPLE 85

2-(4-Chlorophenyl)-4-(2,6-dimethylmorpholino)-6,7-dimethoxyquinazoline (cis/trans Mixture)

M.p.: 165° C.

EXAMPLE 86

2-(4-Chlorophenyl)-4-(3-methoxypropylamino)-6,7-dimethoxyquinazoline

M.p.: 240° C.

EXAMPLE 87

2-(4-Chlorophenyl)-4-(di(2-methoxyethyl)amino)-6,7-dimethoxyquinazoline

M.p.: oil

EXAMPLE 88

2-(4-Chlorophenyl)-4-(4-aminocarbonylpiperidino)-6,7-dimethoxyquinazoline

M.p.: 225° C.

EXAMPLE 89

2-(4-Chlorophenyl)-4-hexamethyleneimino-6,7-dimethoxyquinazoline

M.p.: 189° C.

EXAMPLE 90

2-(4-Chlorophenyl)-4-(cis-2,6-dimethylmorpholino)-6,7-dimethoxyquinazoline

M.p.: 223° C.

EXAMPLE 91

2-(4-Chlorophenyl)-4-(2-hydroxyethylamino)-6,7,8-trimethoxyquinazoline Hydrochloride M.p.: 202° C.

EXAMPLE 92

2-(4-Chlorophenyl)-4-cyclopentylamino-6,7-dimethoxyquinazoline

M.p.: 231° C.

EXAMPLE 93

2-(4-Chlorophenyl)-4-(trans-4-hydroxycyclohexylamino)-6,7-dimethoxyquinazoline

M.p.: 261° C.

EXAMPLE 94

2-(4-Chlorophenyl)-4-(trans-4-hydroxycyclohexylamino)-6,7,8-trimethoxyquinazoline M.p.: 199° C.

EXAMPLE 95

2-(4-Chlorophenyl)-4-(4-hydroxypiperidino)-6,7,8-tdmethoxyquinazoline

M.p.: 176° C.

EXAMPLE 96

2-(4-Methylphenyl)-4-(trans-4-hydroxycyclohexylamino)-6,7-dimethoxyquinazoline

M.p.: 243° C.

EXAMPLE 97

2-(4-Methylphenyl)-4-(N-methyl-N-(3-pyridylmethyl)amino)-6,7-dimethoxyquinazoline M.p.: 165° C.

EXAMPLE 98

2-(4-Methylphenyl)-4-cyclopentylamino-6,7-dimethoxyquinazoline

M.p.: 101° C.

Pharmacological Investigation

Activation of the Soluble Guanylate Cyclase

The activation of the soluble guanylate cyclase (sGC), which catalyzes the conversion of guanosine triphosphate (GTP) into cyclic guanosine monophosphate (cGMP) and pyrophosphate, by the compounds according to the invention was quantified with the aid of an enzyme immunoassay (EIA) from Amersham. For this, the test substances were first incubated with sGC in microtiter plates and then the amount of resulting cGMP was determined. The sGC employed had been isolated from bovine lung (see Methods in Enzymology, Volume 195, p. 377). The test solutions (100 μl per well) contained 50 mM triethanolamine (TEA) buffer (pH 7.5), 3 mM MgCl$_2$, 3 mM reduced glutathione (GSH), 0.1 mM GTP, 1 mM 3-isobutyl-1-methylxanthine (IBMX), suitably diluted enzyme solution and the test substance or, in the case of the control experiments, solvent. The test substances were dissolved in dimethyl sulfoxide (DMSO) and the solution was diluted with DMSO/water such that the final concentration of test substance in the test solution was 50 μM. The DMSO concentration in the test solution was 5% (v/v). The reaction was started by addition of the sGC. The reaction mix was incubated at 37° C. for 15 to 20 minutes and then stopped by ice-cooling and addition of the stop reagent (50 mM EDTA, pH 8.0). An aliquot of 50 μl was taken and employed for the determination of the cGMP content using the acetylation protocol of the Amersham cGMP EIA kit. The absorption of the samples was measured at 450 nm (reference wavelength 620 nm) in a microtiter plate reader. The cGMP concentration was determined by means of a calibration curve which was obtained under the same experimental conditions. The activation of the sGC by a test substance is indicated as n-fold stimulation of the basal enzyme activity which was found in the control experiments (with solvent instead of test substance calculated according to the formula n-fold stimulation=[cGMP]$_{test\ substance}$/[cGMP]$_{control}$).

The following results were obtained.

| Example | n-fold Stimulation | Concentration (μM) |
|---|---|---|
| 09 | 4 | 50 |
| 11 | 6 | 50 |
| 12 | 6 | 50 |
| 13 | 7 | 50 |
| 14 | 3 | 50 |
| 17 | 4 | 50 |
| 20 | 5 | 50 |
| 23 | 4 | 50 |
| 24 | 3 | 50 |
| 25 | 3 | 50 |
| 28 | 5 | 50 |
| 32 | 5 | 50 |
| 33 | 3 | 50 |
| 35 | 5 | 50 |
| 36 | 5 | 50 |
| 37 | 4 | 50 |
| 38 | 7 | 50 |
| 39 | 3 | 50 |
| 42 | 3 | 50 |
| 44 | 4 | 50 |
| 67 | 7 | 50 |
| 79 | 6 | 50 |
| 92 | 6 | 50 |
| 93 | 14 | 50 |
| 94 | 13 | 50 |
| 95 | 7 | 50 |
| 96 | 16 | 50 |
| 98 | 8 | 50 |

What is claimed is:
1. A compound of formula I

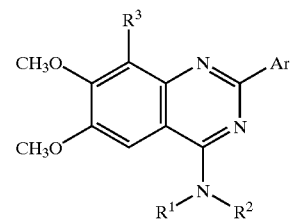

or stereoisomeric forms of the compound of formula I, mixtures of such forms in all ratios, physiologically tolerable salts of the compound of formula I, or mixtures thereof, in which
one of the radicals R$^1$ and R$^2$ is (C$_3$–C$_7$)-cycloalkyl, which is unsubstituted or substituted by
1. (C$_1$–C$_4$)-alkyl,
2. —OH,
3. —O—(C$_1$–C$_4$)-alkyl,
4. —NH$_2$,
and the other of the radicals R$^1$ and R$^2$ is hydrogen, (C$_1$–C$_5$)-alkyl or (C$_3$–C$_7$)-cycloalkyl, wherein the cycloalkyl radical is unsubstituted or substituted by
1. (C$_1$–C$_4$)-alkyl,
2. —OH,
3. —O—(C$_1$–C$_4$)-alkyl,
4. —NH$_2$,
R$^3$ is hydrogen or methoxy,
Ar is phenyl, which is mono-, di- or trisubstituted by
1. halogen,
2. —NO$_2$,
3. —O—(C$_1$–C$_6$)-alkyl,
4. (C$_1$–C$_6$)-alkyl, which is unsubstituted or is mono-, di- or trisubstituted by halogen,
5. —CN,
6. —C(O)—N(R$^{12}$)R$^{13}$, in which R$^{12}$ and R$^{13}$ are identical or different and independently of one another are hydrogen or (C$_1$–C$_6$)-alkyl.
2. One or more compounds of claim 1, in which
one of the radicals R$^1$ and R$^2$ is (C$_3$–C$_7$)-cycloalkyl, which is unsubstituted or substituted by
1. (C$_1$–C$_4$)-alkyl,
2. —OH,
3. —O—(C$_1$–C$_4$)-alkyl,
4. —NH$_2$,
and the other of the radicals R$^1$ and R$^2$ is hydrogen.
3. A compound of formula I

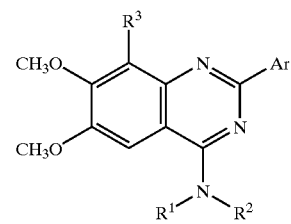

or stereoisomeric forms of the compound of formula I, mixtures of such forms in all ratios, physiologically tolerable salts of the compound of formula I, or mixtures thereof, in which
R$^1$ and R$^2$, together with the N atom to which they are bonded, form a radical of a heterocycle from the group consisting of pyrrole, pyrrolidine, imidazole, pyrazole, piperidine, piperazine, morpholine, pyrazoline, imidazoline, thiomorpholine, thiazolidine, 1-oxothiomorpholine, 1,1-dioxothiomorpholine and hexamethyleneimine, where the heterocycle is unsubstituted or is substituted by
1. —OH,
2. —O—$(C_1-C_6)$-alkyl,
3. —SH,
4. —$SR^4$, in which $R^4$ is $(C_1-C_6)$-alkyl,
5. —$N(R^6)R^7$, in which $R^6$ and $R^7$ are identical or different and independently of one another are hydrogen or $(C_1-C_6)$-alkyl,
6. —C(O)—$N(R^6)R^7$, in which $R^6$ and $R^7$ are identical or different and independently of one another are hydrogen or $(C_1-C_6)$-alkyl, or $R^6$ and $R^7$, together with the N atom to which they are bonded, form a morpholine, piperazine, imidazole, piperidine, pyrrolidine, thiomorpholine, 1-oxothiomorpholine, 1,1-dioxothiomorpholine or hexa-methyleneimine radical,
7. —O—$(C_1-C_6)$-alkyl, which is mono-, di-, or trisubstituted by
   7.1 —OH,
   7.2 —SH,
   7.3 =O,
   7.4 —COOH,
8. —COOH,
9. —C(O)—O—$R^8$, in which $R^8$ is $(C_1-C_6)$-alkyl,
10. phenyl,
11. phenyl, which is mono-, di-, or trisubstituted by
    11.1 —O—$(C_1-C_4)$-alkyl,
    11.2 —O-phenyl,
    11.3 $(C_1-C_4)$-alkyl,
    11.4 —$NO_2$,
    11.5 halogen,
    11.6 —$C(R^9)(R^{10})R^{11}$, in which $R^9$, $R^{10}$ and $R^{11}$ independently of one another are hydrogen or halogen,
12. a radical of a heterocycle from the group consisting of morpholine, piperazine, imidazole, piperidine, pyrrolidine, pyridine, thiomorpholine, 1-oxothiomorpholine, 1,1-dioxothiomorpholine, hexamethyleneimine, pyrrole, pyrazole, pyridazine, pyrazine, pyrimidine, indolizine, indole, indazole, purine, quinoxaline, furan, quinazoline, cinnoline, pteridine, oxazole, isoxazole, thiazole, isothiazole, furazan, indoline, pyrazoline, thiophene, xanthine, imidazoline and pyran,
13. a radical of a heterocycle described in 12, which is mono-, di-, tri-, or tetrasubstituted by
    13.1 $(C_1-C_4)$-alkyl,
    13.2 =O,
    13.3 halogen,
    13.4 —O—$(C_1-C_4)$-alkyl,
    13.5 —$NO_2$,
14. $(C_1-C_6)$-alkyl,
15. $(C_1-C_6)$-alkyl, which is substituted as described under 1, to 13,
$R^3$ is hydrogen or methoxy,
Ar is phenyl, which is mono-, di- or trisubstituted by
1. halogen,
2. —$NO_2$,
3. —O—$(C_1-C_6)$-alkyl,
4. $(C_1-C_6)$-alkyl, which is unsubstituted or is mono-, di- or trisubstituted by halogen,
5. —CN,
6. —C(O)—$N(R^{12})R^{13}$, in which $R^{12}$ and $R^{13}$ are identical or different and independently of one another are hydrogen or $(C_1-C_6)$-alkyl.

4. A method of treating any one of the following conditions or treating a patient susceptible to developing any one of the following conditions of cardiovascular diseases, endothelial dysfunction, diastolic dysfunction, atherosclerosis, high blood pressure, stable or unstable angina pectoris, thromboses, restenoses, myocardial infarcts, strokes, cardiac insufficiency, or pulmonary hypertension, comprising administering to a patient in need of said treatment an effective amount of one or more compounds of claim 1.

5. A method of treating any one of the following conditions or treating a patient susceptible to developing any one of the following conditions of cardiovascular diseases, endothelial dysfunction, diastolic dysfunction, atherosclerosis, high blood pressure, stable or unstable angina pectoris, thromboses, restenoses, myocardial infarcts, strokes, cardiac insufficiency, or pulmonary hypertension, comprising administering to a patient in need of said treatment an effective amount of one or more compounds of claim 3.

6. A process for preparing one or more compounds of claim 1, which comprises reacting a compound of formula VI

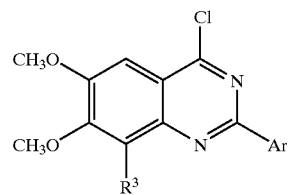

with an amine of formula $HN(R^1)R^2$, where $R^1$, $R^2$, $R^3$ and Ar have the meanings indicated in claim 1.

7. A process for preparing one or more compounds of claim 3, which comprises reacting a compound of formula VI

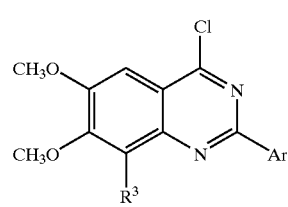

with an amine of formula $HN(R^1)R^2$, where $R^1$, $R^2$, $R^3$ and Ar have the meanings indicated in claim 3.

8. A pharmaceutical composition, which comprises an efficacious amount of one or more compounds of claim 1 with a physiologically tolerable carrier.

9. A pharmaceutical composition, which comprises an efficacious amount of one or more compounds of claim 3 with a physiologically tolerable carrier.

10. A pharmaceutical composition for treating any one of the following conditions or treating a patient susceptible to developing any one of the following conditions of cardiovascular diseases, endothelial dysfunction, diastolic dysfunction, atherosclerosis, high blood pressure, stable or unstable angina pectoris, thromboses, restenoses, myocardial infarcts, strokes, cardiac insufficiency, or pulmonary hypertension, which comprises an efficacious amount of one or more compounds of claim 1 with a physiologically tolerable carrier.

11. A pharmaceutical composition for treating any one of the following conditions or treating a patient susceptible to developing any one of the following conditions of cardiovascular diseases, endothelial dysfunction, diastolic dysfunction, atherosclerosis, high blood pressure, stable or unstable angina pectoris, thromboses, restenoses, myocardial infarcts, strokes, cardiac insufficiency, or pulmonary hypertension, which comprises an efficacious amount of one or more compounds of claim 3 with a physiologically tolerable carrier.

* * * * *